United States Patent [19]
Squillante et al.

[11] Patent Number: 6,106,856
[45] Date of Patent: Aug. 22, 2000

[54] TRANSDERMAL DELIVERY OF CALCIUM CHANNEL BLOCKERS, SUCH AS NIFEDIPINE

[75] Inventors: Emilio Squillante, Coventry, R.I.; Anita Nanda, San Diego, Calif.; Thomas E. Needham; Hossein Zia, both of Wakefield, R.I.

[73] Assignee: The Board of Governors for Higher Education, State of Rhode Island and Providence Plantations, Providence, R.I.

[21] Appl. No.: 08/398,664

[22] Filed: Mar. 3, 1995

Related U.S. Application Data

[63] Continuation-in-part of application No. 08/203,430, Mar. 1, 1994, abandoned.

[51] Int. Cl.[7] .................................................. A61F 13/02
[52] U.S. Cl. ........................... 424/448; 424/449; 514/946
[58] Field of Search .................................. 429/448, 449; 514/946

[56] References Cited

U.S. PATENT DOCUMENTS

| | | | |
|---|---|---|---|
| 4,082,881 | 4/1978 | Chen | 424/241 |
| 4,711,904 | 12/1987 | Luzzi | 514/464 |
| 4,777,047 | 10/1988 | Bauek | 424/449 |
| 4,789,547 | 12/1988 | Song et al. | 424/449 |

*Primary Examiner*—D. Gabrielle Phelan
*Attorney, Agent, or Firm*—Samuels, Gauthier, Stevens & Reppert

[57] ABSTRACT

A transdermal formulation of dihydropyridine calcium antagonists and specifically nifedipine, nimodipine and nitrendipine. The calcium antagonists are dispersed in a mixed liquid. The mixed liquid comprises varying mole fractions of cis-oleic acid and dimethylisosorbide dispersed in a polypropylene glycol base.

14 Claims, 4 Drawing Sheets

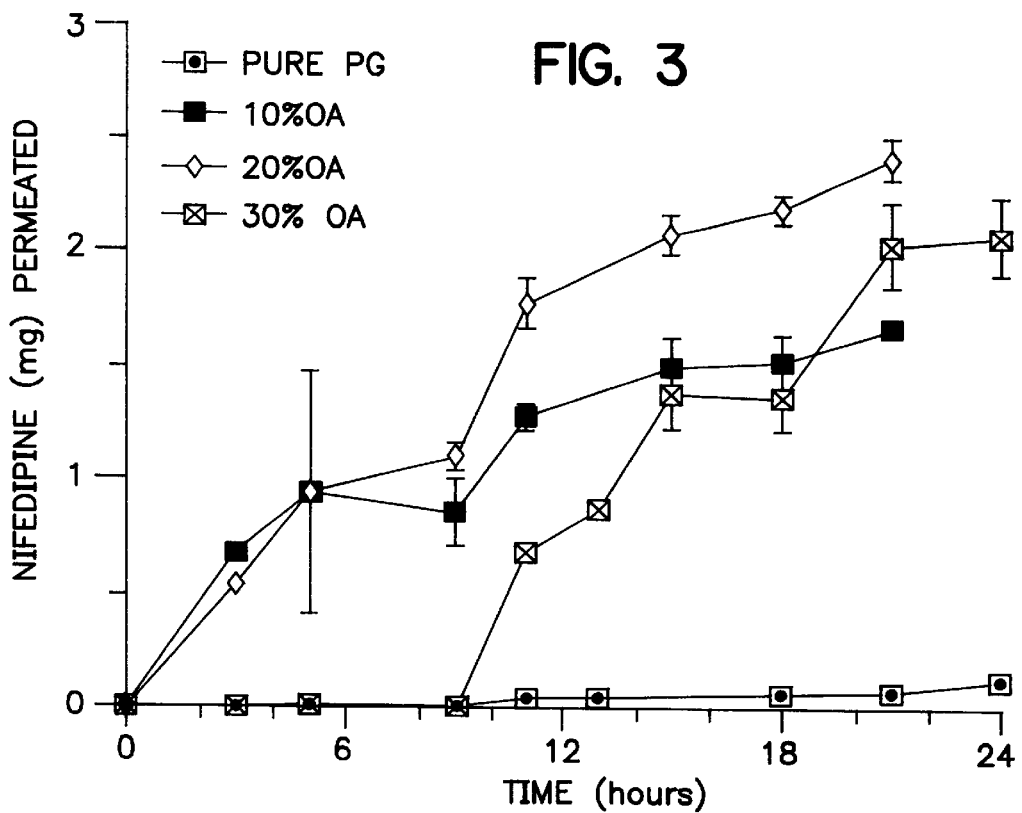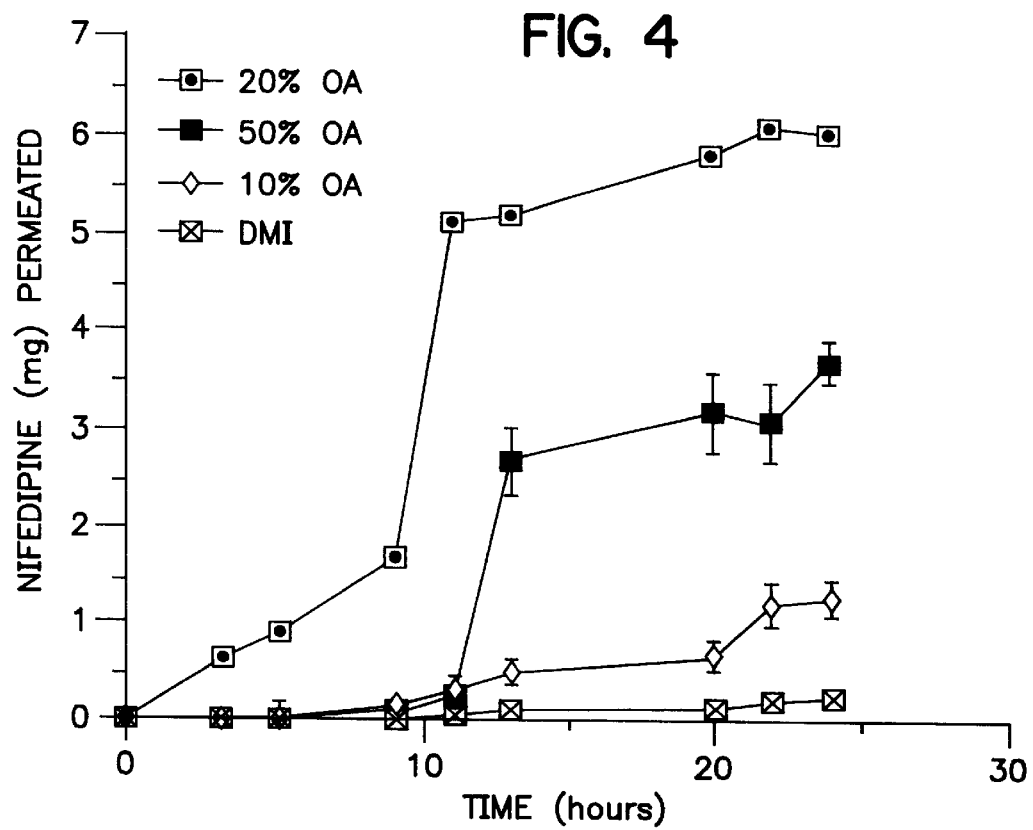

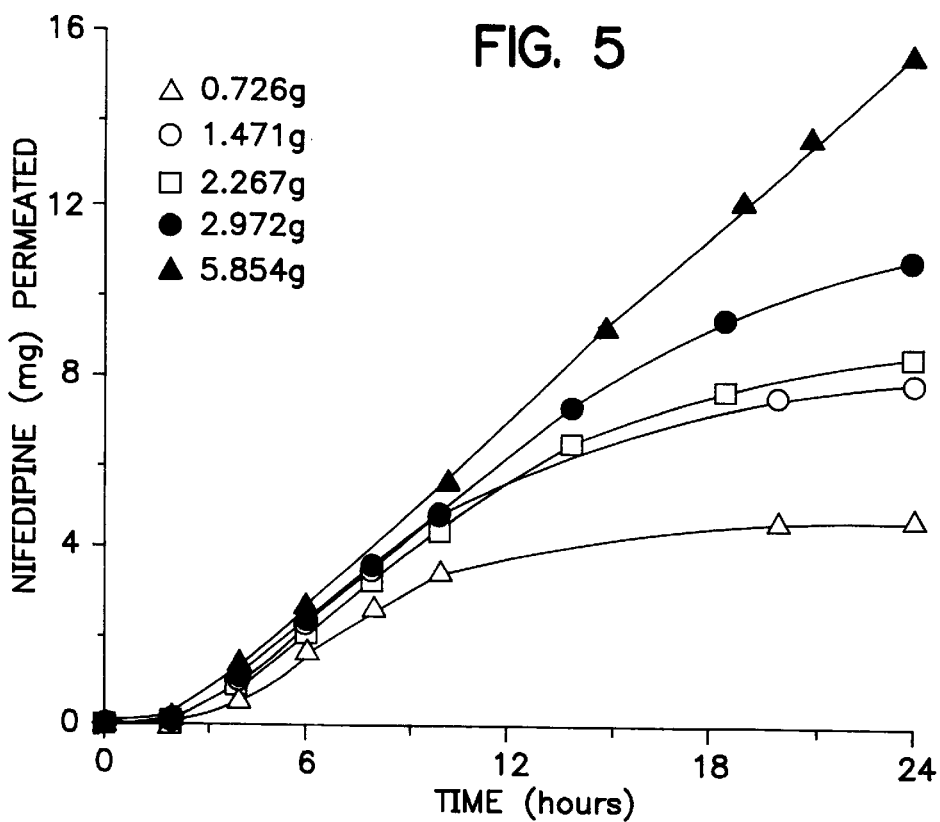
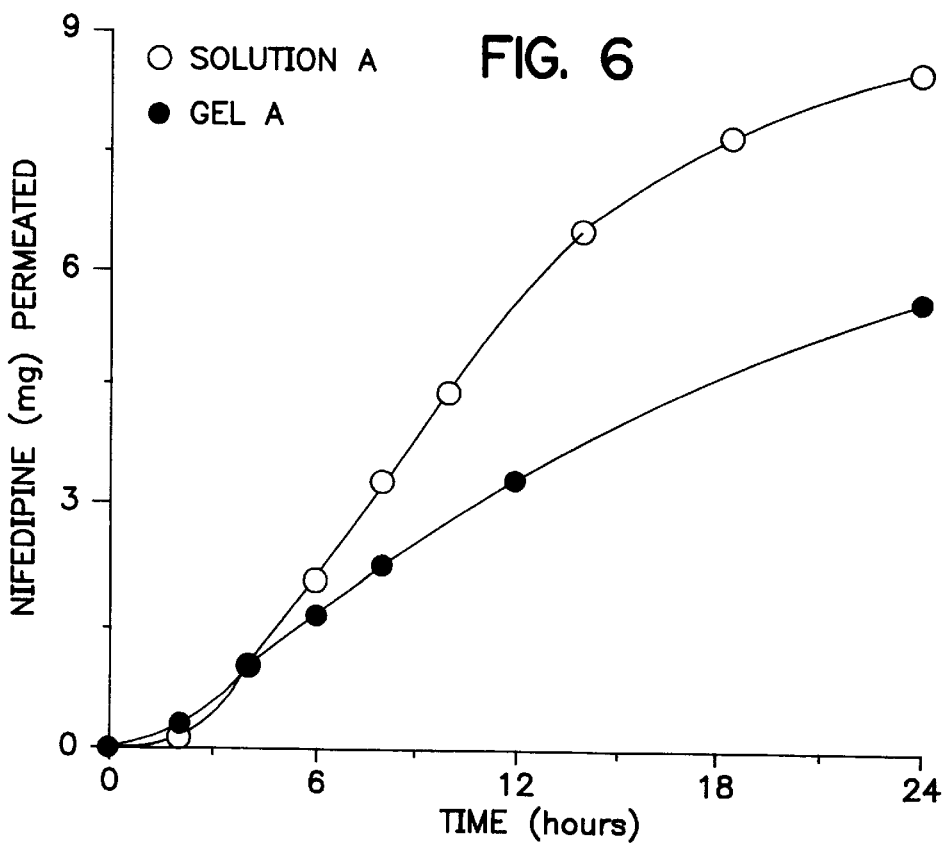

TRANSDERMAL DELIVERY OF CALCIUM CHANNEL BLOCKERS, SUCH AS NIFEDIPINE

This application is a continuation-in-part of Ser. No. 08/203,430 filed Mar. 1, 1994, now abandoned.

FIELD OF THE INVENTION

The invention relates to a novel method of administration of pharmacologically-active dihydropyridine calcium channel blockers, such as nifedipine, to promote the absorption of and effectively raise the concentration of such active substances in the blood stream even when said active substance is one which is usually absorbable through the skin only with considerable difficulty. The rate of absorption of the pharmacologically-active substance through the skin into the blood stream is increased by a novel method of combining cis-oleic acid with solvent vehicles such as propylene glycol and dimethylisosorbide.

DESCRIPTION OF THE PRIOR ART

The potential of skin as a site for the administration of systemically active drugs is evidenced by several commercially successful transdermal delivery systems. Since the early 1980's, several innovative pharmaceutical products have demonstrated the merits of the delivery of therapeutic agents through the skin. Drugs which may be ineffective taken orally may achieve therapeutic concentrations when available in a transdermal delivery system because drugs absorbed percutaneously are not subject to hepatic first pass metabolism. The transdermal route of administration increases compliance by minimizing the inconvenience of remedication which is a decided advantage in conditions, e.g. hypertension, where the effect of the disease is often sublime. Optimally designed transdermal dosage forms release a drug in vivo according to pharmacokinetically rational rates so that serum concentrations are maintained within therapeutically desirable ranges. The net result is a sustained, reliable, extended duration of drug action similar to an intravenous infusion without the many disincentives associated with the intravenous route of administration.

An important feature of transdermal delivery systems is that they permit sustained, constant drug levels over several days. The transdermal route is also appealing since it can reduce problems associated with the aforementioned side effects and thereby improve patient compliance. Nifedipine is an active calcium-channel antagonist accepted as a first line treatment of angina and hypertension, Hansson, L., *Calcium Antagonists: An Overview*, Am. Heart Jour., 1991, 122:1, 308–11; and Dollery, C. T., *Clinical Pharmacology of Calcium Antagonists*, Am. J. of Hypert., 1991, 4, 888–958. Clinical studies have shown that the hypotensive effect as well as untoward side effects are correlated with the plasma nifedipine concentration. When the plasma concentration of nifedipine increases rapidly, there is a marked increase in heart rate and little effect on blood pressure. Conversely, this undesirable situation is reversed when administered by slow intravenous infusion or sustained release tablet, Kleinbloesem, Ch. H.,; van Brummelen, P.; and Breimer, D. D., *Nifedipine. Relationship between pharmacokinetics and Pharmacodynamics*, Clin. Pharmacok, 1987, 12;1, 12–29. Transient, high plasma levels observed following oral administration of conventional capsules may vary by tenfold and increase the likelihood of undesirable high hemodynamic effects, Pasanisi, F.; Merideth, P. A.; Reid, J. L., *Pharmacokinetics of Nifedipine*, Int. J. of Cl. Pharm. Res., 1985, 1, 63–66. Nitroglycerin, the mainstay of anginal therapy, has enjoyed wide acceptance in patch form since once-a-day application contributes significantly towards patient compliance and avoids the large fluctuations in plasma levels following oral administration.

A nifedipine transdermal delivery system of the present invention has the advantage over nitroglycerin transdermal delivery systems in that the constant delivery of nifedipine is not thought to lead to the establishment of tolerance observed in patients treated with nitroglycerin, Reichek, N., *Transdermal Delivery of Nitroglycerin I.*, In Y. W. Chien (ed.), Transdermal Controlled Systemic Medications, Marcel Dekker, NY, 1987, 227–244. In addition to improved convenience and efficacy over other antianginal agents, transdermal nifedipine therapy has a significant margin of safety. Extraordinary interindividual variability of the plasma levels of the drug following oral administration is presumably due to the wide differences in oral bioavailability and the first pass metabolism. Since transdermal administration minimizes pulse entry into the systemic circulation, undesirable side effects associated with unnecessarily high plasma levels of drug can be avoided.

Despite the potential of the skin as a site of administration for systemically active drugs, the transdermal route of administration cannot be employed for all drugs. The skin is an efficient barrier to the ingress of foreign materials so that few drugs penetrate the skin at rates sufficient to permit clinically useful transdermal application. Thus, research efforts targeted toward maximizing penetration have unquestionably strong clinical and financial implications. A need, therefore, exists for strategies that permit rational development of transdermal delivery system. In particular, a need exists for transdermal delivery system compositions which permit adequate nifedipine permeation rates through the skin.

SUMMARY OF THE INVENTION

The invention relates to the treatment of hypertension or angina pectoris by topical application of systemically active drugs. It has been discovered that the permeation of calcium antagonists of the dihydropyridine type, e.g. nifedipine, nimodipine and/or nitrendipine can be enhanced with selected adjuvants.

The term calcium antagonists of the dihydropyridine type is conventionally understood to embrace compounds in a substituted dihydropyridine ring is connected with a substituted benzene ring.

Nifedipine

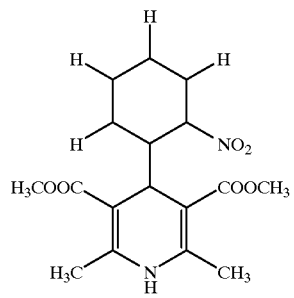

Nimodipine

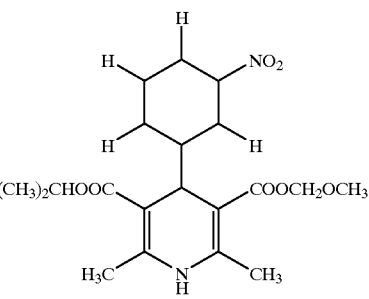

Nitrendipine

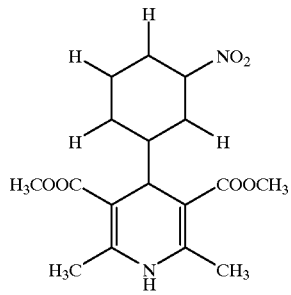

A mixture-type of experimental design and regression techniques are applied to the results of in vitro permeation experiments to: (1) identify the key independent variables that influence the principle responses to be measured; (2) identify both the magnitude and significance of synergism between formulation components; (3) derive a model that predictably describes the shape of the response surface over the simplex factor space; and (4) optimize the desired response. Application of these techniques assisted in the identification of unique blends of adjuvants.

The present invention is a direct result of a novel, stoichiometric approach that interprets, on a molar basis, the influence of permeation enhancers on skin permeability of a selected calcium channel blocker. More specifically the invention relates to calcium antagonists of the dihydropyridine type in combination with a singular blend of cosolvent carrier vehicles composed of various levels of oleic acid, propylene glycol and dimethylisosorbide. The cosolvent carrier vehicle can be applied either directly to the skin surface as a semisolid (gel, cream or paste) or contained in a transdermal delivery system.

It is, accordingly, an object of this invention to provide a method for enhancing the rate of passage of drugs through human skin.

It is another object of the invention to provide compositions of drug-containing formulations which, surprisingly, exert small influence when used alone yet, when combined according to the methods described, have been observed to enhance the rate of passage of nifedipine across the skin.

It is still another object of the invention to provide compositions of adjuvants which are non-toxic and do not exert any physiological effects in the body other than enhancing the rate of passage of drugs across body membranes.

The invention, in one embodiment, comprises the drug nifedipine in combination with a cosolvent carrier vehicle which vehicle comprises adjuvants selected from the group consisting of oleic acid, propylene glycol and dimethylisosorbide.

In a preferred embodiment, the drug formulation is used in combination with a transdermal delivery system.

The preferred embodiment of this invention is directed to a laminated patch equipped with a reservoir that can be loaded with a liquid or semisolid drug: adjuvant mixture described below and an elastomeric matrix material of predetermined thickness and area.

BRIEF DESCRIPTION OF THE DRAWINGS

FIG. 3 graphically shows the amount of nifedipine permeated into the receptor compartment when the donor is composed of nifedipine suspended in propylene glycol to which various mole fraction amounts of cis-oleic acid has been added;

FIG. 4 graphically shows the amount of nifedipine permeated into the receptor compartment over time when the donor is composed of nifedipine suspended in dimethylisosorbide to which various mole fraction amounts of cis-oleic acid has been added;

FIG. 5 graphically shows the influence of amount of donor formulation applied on the amount of nifedipine recovered in the receptor phase as a function of time;

FIG. 6 graphically compares the permeation rates of nifedipine when delivered from a liquid donor versus a similar donor gelled with hydroxypropylcellulose.

DESCRIPTION OF THE PREFERRED EMBODIMENT(S)

Discussion

The evaluation of the compositions of this invention in enhancing the rate of penetration of the drug through a body membrane was carried out in vitro using skin obtained from female hairless mice. Mice (26–28 grams, 8–12 weeks of age, SKH-1) obtained from Charles River Laboratories were sacrificed by cervical dislocation. Whole thickness, intact skin from the ventral region was removed using blunt dissection and immediately mounted between the donor and receptor chambers of a Franz diffusion cell with the stratum corneum exposed to the donor chamber, leaving the dermal side oriented toward the receptor chamber. Four vertical diffusion cells with a surface area of 4.9 cm$^2$ (Crown Glass, Somerville, N.J.) were used for each experiment, keeping one as a control. The receptor phases of the diffusion cells were maintained at 37±0.1° C. Sink conditions were ensured by magnetic stirring of a receptor fluid consisting of a 6:4 (v/v) mixture of normal saline and polyethylene glycol 400 which was replaced periodically as needed.

The detection of suitable cosolvent mixtures was conducted by applying liquid nifedipine:cosolvent suspensions to the donor side of the diffusion cells using a tared syringe. All diffusion cell experiments were run using a suspension of nifedipine in the various vehicles so that the thermodynamic activity of nifedipine would remain constant throughout the study period. A control cell received the donor formulation without a drug therein. The amount of nifedipine in the receptor compartment was determined by HPLC.

The pharmaceutical composition for transdermal administration in accordance with this invention is generally prepared by dispersing a pharmacologically-active substance and other ingredients in a nontoxic, pharmaceutically acceptable liquid base to produce a suspension or gel. The present invention investigated compositions of matter that included cis-oleic acid, dimethylisosorbide and propylene glycol. The contribution of each component in a formula was allowed to vary between 0.1 to 98 mole fraction percent. Typically, higher permeation rates were noticed when a formulation comprised between 1 to 10 mole percent cis-oleic acid and between 1 to 10 mole percent dimethylisosorbide dispersed in propylene glycol. This composition was then introduced into a reservoir compartment and held in place by one of several pressure sensitive adhesives described below.

Figure 1:
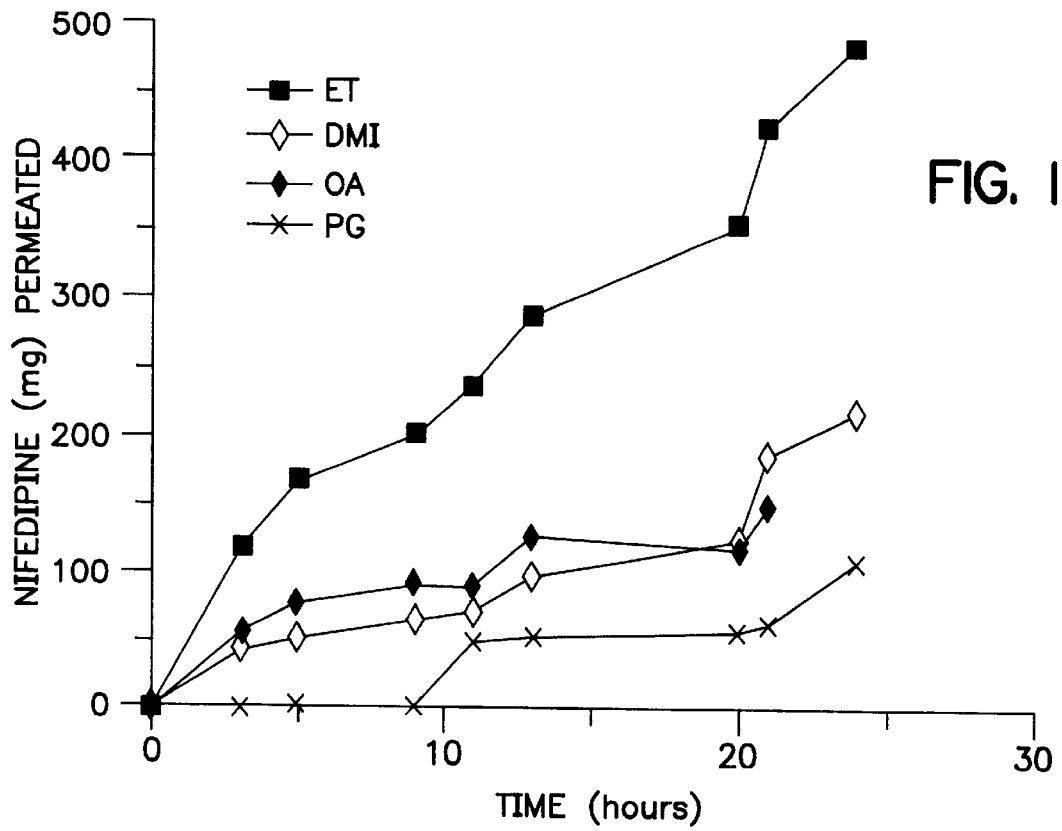
FIG. 1. graphically shows the amount of nifedipine permeated into a receptor compartment over time for a series of pure solvents.

FIG. 1. shows the amount of nifedipine permeated into the receptor compartment over time for a series of pure solvents, specifically, cis-oleic acid (OA), dimethyl isosorbide (DMI), ethanol (ET) and propylene glycol (PG). The donor is composed of nifedipine suspended in each of the pure solvents. Additional amounts of nifedipine are added so that the total amount of drug exceeds its saturation solubility by 10%. Permeation is comparatively poor and these solvents, when applied individually, cannot deliver a clinically useful amount of nifedipine. For purposes of this disclosure clinically useful amount means 18 milligrams in a 24 hour period.

Figure 2:
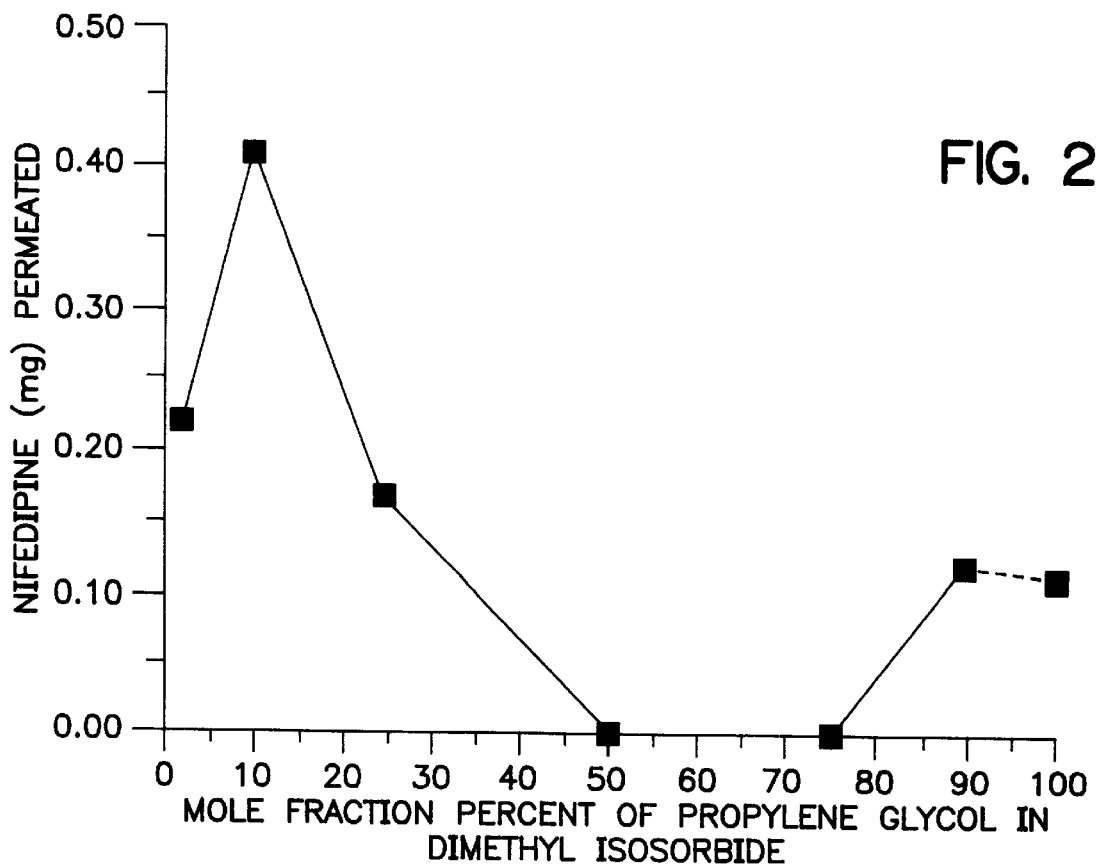
FIG. 2 graphically shows the total amount of nifepidine permeated into the receptor compartment after a 24 hour period when the donor is composed of nifedipine suspended in binary mixtures.

FIG. 2 shows the total amount of nifepidine permeated into the receptor compartment after a 24 hour period when the donor is composed of nifedipine suspended in binary mixtures of dimethyl isosorbide (DMI) to which various mole fraction amounts of propylene glycol (PG) have been added. Although nifedipine has good solubility in both vehicles, the binary mixtures cannot deliver clinically useful amounts of nifedipine.

FIG. 3 shows the amount of nifedipine permeated into the receptor chamber when the donor is composed of nifedipine suspended in propylene glycol (PG) to which various mole fraction amounts of cis-oleic acid (OA) have been added. The combination of the enhancer (OA), when combined with a good solvent for nifedipine (PG), improved the permeation of drug, but the amount delivered still remains below clinically useful quantities.

FIG. 4 shows the amount of nifedipine permeated into the receptor compartment over time when the donor is composed of nifedipine suspended in dimethylisosorbide (DMI) to which various mole fraction amounts of cis-oleic acid (OA) has been added. Once again, the combination of an enhancer (OA) with a good solvent for nifedipine (DMI), improves the performance of donor. In both FIGS. 3 and 4, it is noteworthy that the effect on nifedipine permeation rates is maximal at around 20% mole fraction percent OA, after which higher concentrations of OA impede nifedipine permeation.

FIG. 5 shows the amount of nifedipine permeated into the receptor compartment and the amount of nifedipine recovered in the receptor phase as a function of time, for various amounts of the donor formulations applied directly to the skin. The donor is a quaternary mixture of cis-oleic acid, dimethylisosorbide, ethanol and propylene glycol that demonstrate adequate nifedipine permeation rates which are sustained for 24 hours at the highest does.

FIG. 6 compares the permeation rates of nifedipine when delivered from a liquid donor versus a similar donor gelled with hydroxypropylcellulose under the conditions specified in example 1. (The gel formulation was applied to the skin from sponge-like delivery devices as described in Example 1).

FIG. 6 shows that a gelling agent may be employed to effectively control the properties of the invention, thereby controlling the release of active agent from the dosage form.

Figure 7:
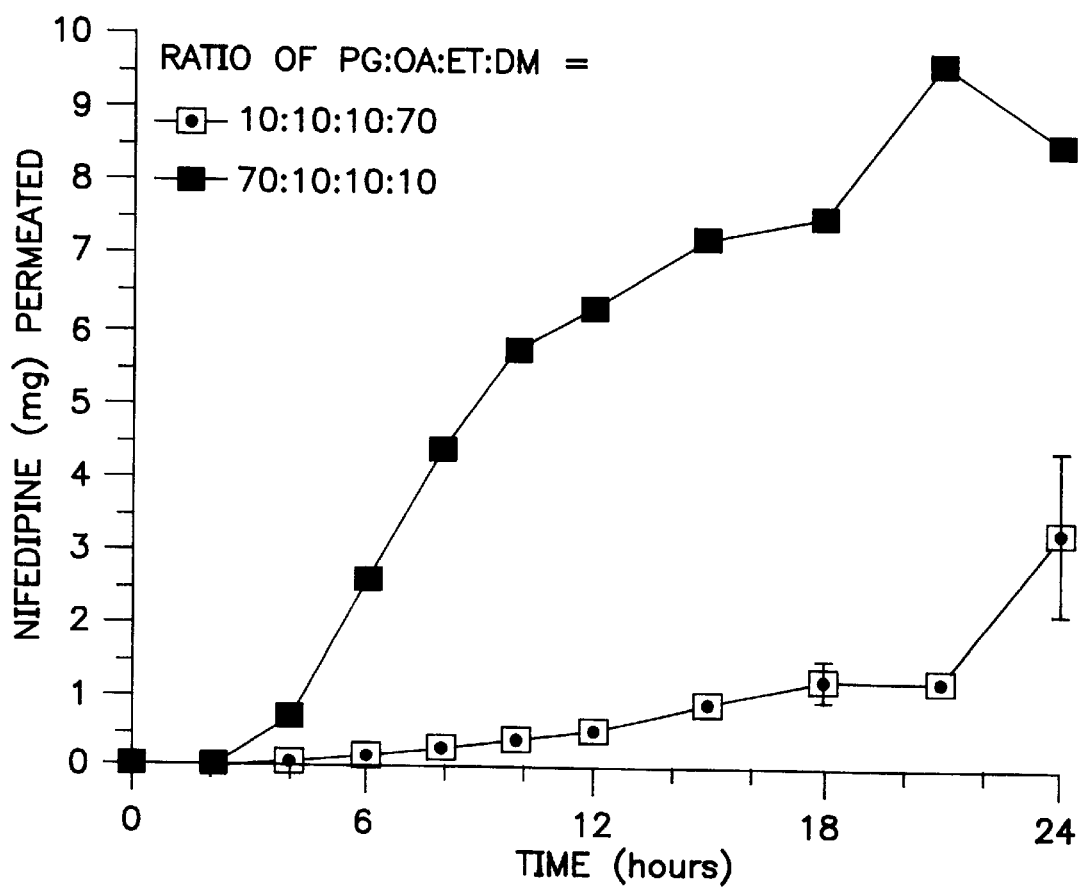
FIG. 7 graphically shows permeation rates from a quaternary cosolvent mixture.

For FIG. 7, the donor was prepared as before except that ethanol was added to form a quaternary cosolvent mixture. These mixtures were prepared by holding the ratio of OA to ET constant at 10% and allowing the proportion of PG and DMI to vary between 1 to 79%. In a series of optimization experiments, only two of which are displayed, it was discovered that flux and lag time are controlled by the ratio of propylene glycol (PG) to dimethyl isosorbide (DMI), with high levels of DMI yielding poor flux and unacceptable lag times. An unexpected result of these inquires was that ethanol had no significant effect on overall performance, allowing the present invention to be simplified to a ternary system consisting of OA and DMI in excess PG.

In summary, FIGS. 1–4 provide a frame of reference to highlight the superior performance exhibited by the ternary vehicle represented in FIGS. 5 and 6. Collectively, the figures clearly demonstrate the unexpected, significant synergistic effect that this composition of matter, embodied in the present invention, has on the potential for delivery of clinically useful amount of nifedipine in humans.

EXAMPLE 1

Prototype Transdermal Delivery Devices

The cosolvent vehicles were composed of 1% dimethylisosorbide, 10% oleic acid, 1% ethanol and 88% propylene glycol expressed as mole percent which correspond in weight percent to 1.8% DMI, 29% OA, 0.4% ET and 68.8& PG respectively. Increasing amounts of donors were applied in direct contact with the mounted skin on the donor side of a Franz cell. A sponge-like pad in the center of the device acts as a reservoir for the gels and this pad is held in place by an adhesive overlay. It was found that at the end of the study period the rate of passage of nifedipine through excised mouse skin exceeded that needed to deliver an equivalent oral dose. Specifically, a formulation of 1% DMI, 10% OA, 1% ET, and 88% PG (mole percent) caused nifedipine to permeate the skin at a rate of 146 $\mu g/hr/cm^2$ over 2–24 hours.

EXAMPLE 2

Pressure Sensitive Adhesive Film Preparation

The polymer substrates, being dispersions of monomer in a volatile carrier, are expressed in terms of weight of solids. The pressure sensitive adhesives evaluated were: (1) silicone X7-4301 and X7-2920 (Dow Corning); (2) polystyrene-block-polyisoprene-block-polystyrene (PIB) of 15:85 styrene/rubber ratio (Shell Schweiz AG, CH Zurich); (3) polyacrylic DURO-TAK 120-1753 (PA) crosslinked with 4% w/w aluminum acetyl acetonitrile (National Starch and Chemical Company, Bridgewater, N.J.); and (4) ethyl:vinyl acetate hot melt (EVA) (33:400/28:800) hot-melt mixtures with 5% Cetiosol S (Scheller AG, CH-Zurich).

In addition to the vehicles noted in Example One, azone (Whitby Research, Richmond, Va. 23261) and isopropyl myristate (Sigma Chemicals) were also evaluated. The relative effects of propylene glycol, cis-oleic acid, ethanol, dimethylisosorbide, azone and isopropyl myristate on nifedipine permeation were evaluated by blending equimolar amounts of these components to form the fifteen possible quaternary cosolvent vehicles. Sufficient nifedipine was added to each blend to insure that drug is present in levels that exceed nifedipine saturation solubility by 10%.

The stock liquid drug:cosolvent mixtures were added incrementally to the liquid pressure sensitive adhesives, mixed for 10 minutes and then applied as films to polyester backing layers (3M Company). The films were prepared in thicknesses between 50 and 200 microns in a suspended-knife apparatus. Removal of residual solvent was accomplished by evaporation in a ventilated oven set at 60° C. for 20 minutes. The films were then laminated onto a foil release liner and stored under ambient conditions. Screening of pressure sensitive adhesive films were carried out by measurement of penetration rates through freshly excised hairless mouse skins mounted in Franz cells to evaluate their suitability in the prototype delivery devices. The best four way permutation of the fifteen possible equimolar quaternary mixtures, in terms of flux and lag time, proved to propylene glycol:cis-oleic acid:ethanol:dimethyl isosorbide.

EXAMPLE 3

Reservoir Device Preparation

The present invention represents a valuable alternative in that the drug:cosolvent mixture is not subjected to the deleterious effect of high temperatures required by solvent-based and hot-melt coating processes. Processing at elevated temperatures can be executed prior to the addition of heat-sensitive components. This is accomplished by the formulation of the pressure sensitive adhesive films and their subsequent lamination, at room temperature to a layer incorporating the drug and enhancers.

In vitro skin permeation profiles of nifedipine under the influence of selected penetration enhancers from adhesive matrix devices were evaluated using excised hairless mouse skin. Prototype devices containing permeation and enhancers were prepared from silicone adhesives, silicone elastomer, pressure sensitive acrylic, and polystyrene-block-polyisoprene-block-polystyrene pressure sensitive adhesives (PSA). Since the release of drug from the thin films prepared in Example 2 was poor, a semi-porous membrane was used to immobilize the drug:cosolvent mixture in a pouch-like reservoir that preferably utilizes a silicone elastomer as the pressure sensitive adhesive matrix. Reservoir-type devices thus formed were evaluated to deliver drug and enhancer to the skin.

The reservoir devices utilized are composed of four basic components: an impermeable backing, an adhesive, a drug reservoir, and a microporous membrane to contain the drug suspended in vehicle. Polypropylene membrane at 38% porosity (Celgard 2400 Celanese Separations Products, Charlotte, N.C. 28232) is the retaining membrane. Scotch-pack heatsealable, polyester film laminate (No. 1022, 3M Company) comprises the backing layer. The patches of the present invention preferably utilize a silicone elastomer, e.g. X7-2920 and X7-4301 (Dow Corning) as the matrix. Silicone pressure sensitive adhesive films, e.g. X7-4301 is applied to the release liner (polyester film No. 9747, 3M Company), a layer of Celgard is placed atop the pressure sensitive adhesive and heat sealed using a die compressed for 13 seconds at 70° C. to form a patch with a reservoir between the Celgard and backing layer. The patch reservoir is loaded by inserting a hypodermic syringe into the orifice leading into the reservoir chamber, expressing 0.3 ml of the drug:cosolvent heating mixture and then sealing the orifice. Patches are stored for one week prior to testing to allow the reservoir components to equilibrate with the pressure sensitive adhesive. The adhesive laminates are placed on the excised skin, a 200 gram weight placed atop for 2 minutes, and then mounted in the Franz cell.

The silicone pressure sensitive adhesive tested retains a suitable degree of tack for initial bonding, leaves no residue when removed, conforms to skin contours and accommodates skin movement to hold the transdermal delivery system in place for several days, and sufficient cohesive strength is observed.

The two measured responses of interest (i.e. flux and lag time) are derived from the profiles obtained by plotting the steady state nifedipine permeation as a function of time. The flux is quantified from the slope and the lag time from the point of intersection with the abscissa of the back extrapolated portion of these curves.

EXAMPLE 4

Following the procedures described above, 1.7 g of nimodipine was dissolved in 100 g of a solvent mixture (27, 1 g oleic acid, 10 g DMI and 61, 3 g propylene glycol). 1 m of this solution was given on heat-separated human epidermis (female breast, age 51 years, area 4.5 cm$^2$) which was mounted on a Franz-diffusion cell. The cell was filled with 23 ml of a mixture of 60 parts of a 0.9% NaCl-solution and 40 parts of polyethylene glycol 400 (v/v). At the sampling times the receptor fluid is completely renewed and analyzed for nimodipine content.

| | Cumulated Amount Permeated Drug ($\mu$g/cm$^2$) | | | | |
|---|---|---|---|---|---|
| Formulation | 8 h | 24 h | 32 h | 48 h | Comments |
| Nimodipine | 2.2 | 214.3 | 329.9 | 388.8 | saturated solution, |
| | 5.3 | 317.5 | 433.7 | 473.5 | applied crystal-free |
| | 0.5 | 23.7 | 37.3 | 137.2 | recrystallization during |
| mean | 2.7 | 185.2 | 267.0 | 333.2 | the experiment |
| Flux ($\mu$g/cm *h) | 0.34 | 11.41 | 10.23 | 4.14 | Epidermis |
| Nifedipine | 3.6 | 248.7 | 473.4 | 587.2 | saturated solution, |
| | 0.2 | 5.0 | 22.7 | 181.2 | applied crystal-free |
| | 4.6 | 111.8 | 163.3 | 245.6 | recrystallization during |
| mean | 2.8 | 121.8 | 219.8 | 416.4 | the experiment |
| Flux ($\mu$g/cm *h) | 0.35 | 7.44 | 6.13 | 12.29 | Epidermis |

The distinguishing feature of the mixture design is that the independent, controllable factors represent proportionate amounts of the mixture rather than unrestrained amount. These restrictions limit the manner in which an investigator may: (1) choose the proportions of the ingredients; (2) analyze the data collected from experiments; and (3) interpret the results of the analysis to permit mole fraction comparisons between patch components. Due to practical considerations such as cost, irritancy and stability, valid mixtures must contain a component in some minimum amount $a_i$ and maximum amount $c_i$. The proportion $x_i$ of component i must be bounded below by $a_i > 0$ and above by $c_i < 1.0$. The quantity $a_i$ is known as the 'lower bound', $c_i$ the 'upper bound', and in addition to usual constraints, $x_i \geq 0$, $X_1 + X_2 + \ldots + X_q = 1$, a second limitation for the constrained simplex is 0, $< a_i \leq X_i \leq C_i \leq 1$, i=1,2, ..., q The effective donor formulations must contain relative proportions of the components restricted to the following upper, $c_i$, and lower, $a_i$, bounds; $0.1\% < x_1 < 97\%$; $0.1\% < x_3 < 30\%$; $0.1\% < x_2 \times 30\%$; and $0.1\% < x_4 < 30\%$ where, for the present invention, propylene glycol=$(x_1)$, cis-oleic acid=$(x_2)$, ethanol=$(x_3)$, and dimethylisosorbide=$(x_4)$.

As this invention may be embodied in several forms without departing from the spirit or essential characteristics thereof, the preferred embodiment(s) is therefore illustrative and not restrictive, since the scope of the invention is defined by the appended claims rather than by the description preceding them, and all changes that fall within the metes and bounds of the claims or that form their functional as well as conjointly cooperative equivalents, are therefore intended to be embraced by these claims.

Having described my invention,

What I now claim is:

1. A transdermal formulation which consists of dihydropyridine calcium antagonists selected from the group consisting of nifedipine, nimodipine or nitrendipine and 1 to 20% weight percent of dihydropyridine dissolved or undissolved calcium antagonist in a mixed liquid, the mixed liquid comprising 0.1 to 50% mole fraction percent cis-oleic acid and between 0.1 and 97 mole fraction percent dimethylisosorbide dispersed in a propylene glycol base.

2. A transdermal formulation of calcium antagonists as claimed in claim 1, wherein the calcium antagonist is nifedipine.

3. A transdermal formulation of calcium antagonists as claimed in claim 1, wherein the mixture of the liquids contains up to 97 mole fraction percent ethanol.

4. A transdermal formulation as claimed in claim 3, wherein the formulation is contained in a device comprising an impermeable backing and a drug releasing side adapted to be brought in contact with the skin during application.

5. A transdermal formulation as claimed in claim 4, wherein the drug releasing side of the device is at least partly provided with a pressure sensitive self-adhesive layer to fix the device on the skin.

6. A transdermal formulation of calcium antagonists as claimed in claim 1, which comprises:

a thickening agent to gel the mixed liquid.

7. A transdermal formulation of calcium antagonists as claimed in claim 6, wherein the thickening agent comprises 0.1 to 10% by weight of hydroxypropylcellulose.

8. A transdermal formulation of calcium antagonists as claimed in claim 6, wherein the thickening agent comprises 0.1 to 10% by weight of hydroxypropylcellulose and glycerol.

9. A transdermal formulation of calcium antagonists as claimed in claim 6, wherein the thickening agent comprises 0.1 to 10% by weight of a compound selected from the group consisting of hydroxypropylcellulose, polyethylene glycol 400, cetyl alcohol or strearyl alcohol.

10. A transdermal formulation as claimed in claim 6, wherein the formulation is contained in a device comprising an impermeable backing and a drug releasing side adapted to be brought in contact with the skin during application.

11. A transdermal formulation as claimed in claim 10, wherein the drug releasing side of the device is at least partly provided with a pressure sensitive self-adhesive layer to fix the device on the skin.

12. A transdermal formulation as claimed in claim 1, wherein the formulation is contained in a device comprising an impermeable backing and a drug releasing side adopted to be brought in contact with the skin during application.

13. A transdermal formulation as claimed in claim 12, wherein the drug releasing side of the device is at least partly provided with a pressure sensitive self-adhesive layer to fix the device on the skin.

14. A transdermal formulation of calcium antagonists as claimed in claim 1, wherein the calcium antagonist is nimodipine.

* * * * *